United States Patent
Wosnick et al.

(10) Patent No.: US 9,405,207 B2
(45) Date of Patent: Aug. 2, 2016

(54) TONER COMPOSITIONS

(71) Applicant: Xerox Corporation, Norwalk, CT (US)

(72) Inventors: Jordan H Wosnick, Toronto (CA);
Santiago Faucher, Oakville (CA);
Edward G Zwartz, Mississauga (CA);
Michael S Hawkins, Cambridge (CA);
Karen A Moffat, Brantford (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 14/492,003

(22) Filed: Sep. 20, 2014

(65) Prior Publication Data
US 2015/0010336 A1  Jan. 8, 2015

Related U.S. Application Data
(63) Continuation of application No. 12/625,617, filed on Nov. 25, 2009, now abandoned.

(51) Int. Cl.
| | | |
|---|---|---|
| *G03G 9/087* | (2006.01) | |
| *G03G 15/20* | (2006.01) | |
| *G03G 9/093* | (2006.01) | |
| *C12P 7/62* | (2006.01) | |

(52) U.S. Cl.
CPC ............ *G03G 9/08755* (2013.01); *C12P 7/62* (2013.01); *G03G 9/08795* (2013.01); *G03G 9/08797* (2013.01); *G03G 9/09371* (2013.01); *G03G 15/2064* (2013.01); *G03G 2215/20* (2013.01)

(58) Field of Classification Search
CPC .......... G03G 9/08755; G03G 9/08795; G03G 9/08797; G03G 9/09371; G03G 2215/20; C12P 7/62
USPC ........ 430/124.1, 124.23, 124.3, 109.1, 109.4; 399/252, 318, 328, 330, 331
See application file for complete search history.

(56) References Cited

U.S. PATENT DOCUMENTS

| | | | |
|---|---|---|---|
| 4,339,194 A * | 7/1982 | Scribner | G03G 15/2092 100/172 |
| 4,958,195 A | 9/1990 | Firth et al. | |
| 5,981,240 A | 11/1999 | Akkara | |
| 6,821,698 B2 | 11/2004 | Sawada et al. | |
| 2005/0255397 A1 | 11/2005 | Yamamoto et al. | |
| 2007/0296122 A1* | 12/2007 | Chen | G03G 15/2057 264/346 |
| 2009/0011347 A1 | 1/2009 | Daimon et al. | |
| 2010/0055750 A1 | 3/2010 | Wosnick | |

* cited by examiner

*Primary Examiner* — Thorl Chea (57) ABSTRACT

The present disclosure provides for enzymatic polymerization to produce polyester resins suitable for use in manufacturing toners. In embodiments, crystalline copolymers, which are polyesters, may be synthesized from lactones, cyclic anhydrides, cyclic carbonates, and combinations thereof. These crystalline copolymers, in turn, may be utilized in the synthesis of toner particles.

4 Claims, 2 Drawing Sheets

TONER COMPOSITIONS

BACKGROUND

The present disclosure is generally directed to polyester synthesis processes and, more specifically, to processes for the enzymatic synthesis of polyester resins which may be utilized in the formation of toners, and in particular, emulsion aggregation toners.

Electrophotographic printing utilizes toner particles which may be produced by a variety of processes. One such process includes an emulsion aggregation ("EA") process that forms toner particles in which surfactants are used in forming a latex emulsion. See, for example, U.S. Pat. No. 6,120,967, the disclosure of which is hereby incorporated by reference in its entirety, as one example of such a process.

Combinations of amorphous and crystalline polyesters may be used in the EA process. This resin combination provides toners with high gloss and relatively low-melting point characteristics (sometimes referred to as low-melt, ultra low melt, or ULM), which allows for more energy efficient and faster printing. Poor crystalline-amorphous polymer combinations may result in toners that either do not show low-melt behavior or exhibit unacceptable heat cohesion properties. Low-melt polyester toners may thus rely upon a sharp-melting crystalline resin component to provide the low-melt behavior.

Crystalline polyesters may be prepared by the polycondensation of linear, aliphatic diacids and diols present in the polymer at a 1:1 molar ratio. The range of compatibility for crystalline materials with the amorphous components of a low-melt polyester toner may be very narrow; crystalline polymers that fall outside of this range give toners with either no low-melt properties or excessive temperature instability. Even slight modifications to the chemical structure of a crystalline polyester, such as the extension of either the diacid or the diol unit by one carbon atom, can result in dramatic changes to the polyester's solubility and thermodynamic properties, including its melting properties, and render it useless for a low-melt polyester toner. Moreover, these polyester resins have been synthesized by high-temperature polycondensation using metal catalysts. The presence of these catalysts in the final toner, combined with the energy required for polycondensation, represent environmental challenges. Therefore, there is a continual need for improving polyester resins synthesis. It is further desired to produce a toner with low gloss. In addition, it is desired to produce a toner that can be used in cold pressure fusing.

SUMMARY

The present disclosure provides processes for producing polyesters, in embodiments crystalline polyesters, and the use of same in forming toner particles.

In embodiments, a process of the present disclosure may include contacting at least one component such as lactones, lactides, cyclic anhydrides, cyclic carbonates, and combinations thereof, with an enzyme such as lipases, cutinases, and combinations thereat polymerizing the at least one component to form a crystalline polyester resin; recovering the crystalline polyester resin; contacting the crystalline polyester resin with an optional amorphous resin, an optional colorant, an optional wax, and an optional surfactant to form toner particles; and recovering the toner particles, wherein the toner particles are suitable for cold pressure fusing.

In other embodiments, a process of the present disclosure may include contacting at least one component such as lactones, lactides, cyclic anhydrides, cyclic carbonates, and combinations thereof, with an enzyme such as lipases, cutinases, and combinations thereof; polymerizing the at least one components to form a crystalline polyester resin; recovering the crystalline polyester resin; contacting the crystalline polyester resin with an optional amorphous resin, an optional colorant, an optional wax, and an optional surfactant to form toner particles; recovering the toner particles; applying the toner particles to a substrate; and fixing the toner particles to the substrate at a temperature of from about 20° C. to about 50° C. by application of pressure of from about 3 kpsi to about 10 kpsi.

An apparatus suitable for use with toners of the present disclosure is also provided. In embodiments, such an apparatus may include a toner source; and a fuser including a fuser roll member capable of applying pressure of from about 3 kpsi to about 10 kpsi thereby fixing the toner onto an image receiving substrate at a temperature of from about 10° C. to about 80° C., wherein the toner includes at least one amorphous polyester resin, an optional colorant, an optional wax, and at least one crystalline polyester resin, the at least one crystalline polyester resin formed by contacting at least one component such as lactones, lactides, cyclic anhydrides, cyclic carbonates, and combinations thereof with an enzyme such as lipases, cutinases, and combinations thereof.

BRIEF DESCRIPTION OF THE DRAWINGS

Various embodiments of the present disclosure will be described herein below with reference to the figures wherein.

DETAILED DESCRIPTION

The present disclosure relates to enzymatic polymerization processes for the production of resins suitable for use in the formation of toners. In embodiments, processes of the present disclosure may be utilized to produce crystalline polyester resins with organically derived catalysts. The present toners provide for relatively low gloss, and can be used in cold-pressure fusing electrophotographic apparatii.

In embodiments, the present disclosure provides methods for the preparation of crystalline and semi-crystalline polyesters with melting points suitable for use as a low-melt polyester toner, in embodiments from about 55° C. to about 95° C., in other embodiments from about 65° C. to about 85° C. The melting points of these crystalline and semi-crystalline polyesters, which may be prepared by enzymatic ring-opening co-polymerization of large-ring macrocyclic lactones, cyclic anhydrides, cyclic carbonates, and combinations thereof, can be controlled with an unexpected degree of precision by making fine adjustments to the monomer feed ratios. Unlike polyesters prepared by condensation of diacids and diols, an infinite range of compositions may thus be prepared from the same pair of starting monomers. Exemplary materials include those disclosed in U.S. patent application Ser. No. 12/203,169, filed Sep. 3, 2008, the disclosure of which is hereby incorporated by reference in its entirety.

Resins

Any monomer or starting material suitable for preparing a latex for use in a toner may be utilized. In embodiments, the resin of the latex may include at least one polymer. In embodiments, at least one polymer may be from about one to about twenty and, in embodiments, from about three to about ten. Suitable resins include polyester resins, including the resins described in U.S. Pat. Nos. 6,593,049 and 6,756,176, the disclosures of each of which are hereby incorporated by reference in their entirety. Suitable resins may also include a mixture of an amorphous polyester resin and a crystalline polyester resin as described in U.S. Pat. No. 6,830,860, the disclosure of which is hereby incorporated by reference in its entirety. In embodiments of the present disclosure, the amorphous resin may be formed by emulsion polymerization methods, and the crystalline resin may be formed by enzymatic polymerization of a lactone, cyclic anhydride, and/or cyclic carbonate.

In embodiments, crystalline polyesters utilized in forming the resins may be obtained from the enzymatic polymerization of lactones, cyclic anhydrides, and/or cyclic carbonates. In embodiments, the crystalline polyesters obtained may be copolymers obtained by the ring-opening polymerization of two or more lactones, cyclic anhydrides, and/or cyclic carbonates. Suitable lactones include 6-, 12-, 13-, 16-, and 17-membered lactones or macrolides.

In embodiments, suitable starting materials for forming the resins include lactones based upon caprolactone, pentadecalactone (sometimes referred to herein as PDL, commercially available as EXALTOLIDE® from Firmenich), pentadecenlactone, including mixtures of 12-13 and cis-trans isomers of pentadecenlactone (sometimes referred to as 11/12-pentadecen-15-olide, commercially available as HABANOLIDE® from Firmenich), hexadecenlactone, 7-Hexadecen-16-olide (sometimes referred to herein as HDEL, commercially available as AMBRETTOLIDE from SAFC™, sold exclusively by Sigma Aldrich), dodecalactone, combinations thereof, and the like.

Unlike conventional polyesters, where diacid units and diol units may be present in a polymer in equimolar quantities, lactones containing both acid- and alcohol functionality may be co-polymerized in any desired ratio. Accordingly, co-polymers of the structurally similar lactones pentadecalactone and pentadecenlactone may be prepared by enzymatic ring-opening polymerization to form semi-crystalline polyesters with melting points intermediate between those of the corresponding homopolymers.

In other embodiments, crystalline polyesters utilized in forming the resins may be obtained from the enzymatic polymerization of cyclic anhydrides, cyclic carbonates, combinations thereof, optionally combined with lactones described above, and the like. Suitable cyclic anhydrides include, but are not limited to, aliphatic dicarboxylic anhydrides and aromatic dicarboxylic anhydrides. Examples of aliphatic dicarboxylic anhydrides include succinic anhydride, glutaconic anhydride, maleic anhydride, cyclopentane-1,2-dicarboxylic anhydride, cyclohexene-1,2-dicarboxylic anhydride and 2,3-bicyclo[2,2,2]octadicarboxylic anhydride. Examples of aromatic dicarboxylic anhydrides include phthalic anhydride, naphthalene-dicarboxylic anhydride, pyridine-dicarboxylic anhydride and thiophene-dicarboxylic anhydride.

Suitable cyclic carbonates include, but are not limited to, trimethylene carbonate, carboxy-trimethylene carbonate and esters thereof, combinations thereof, and the like.

In embodiments, the crystalline polyesters obtained may be copolymers obtained by the ring-opening polymerization of two or more cyclic anhydrides, two or more cyclic carbonates, or any combination of monomers obtained by the ring-opening polymerization of lactones, cyclic anhydrides, cyclic carbonates, and the like.

The resulting copolymers, for example, copolymers of the lactones, anhydrides, carbonates, or combinations thereof, including copolymers of poly(pentadecalactone) with poly (pentadecenlactone), and the like, may have a molecular weight of about 2,000 or above, in embodiments from about 5,000 to about 50,000, in embodiments from about 7,000 to about 30,000.

The first monomer may be present in a copolymer in accordance with the present disclosure in an amount of from about 0.5% by weight of the copolymer to about 99.5% by weight of the copolymer, in embodiments from about 10% by weight of the copolymer to about 90% by weight of the copolymer, with the second monomer present in an amount of from about 99.5% by weight of the copolymer to about 0.5% by weight of the copolymer, in embodiments from about 90% by weight of the copolymer to about 10% by weight of the copolymer.

The crystalline resins thus produced can possess various melting points of, for example, from about 55° C. to about 95° C., in embodiments from about 65° C. to about 85° C. The crystalline resins may have a number average molecular weight ($M_n$), as measured by gel permeation chromatography (GPC) of, for example, from about 1,000 to about 50,000, in embodiments from about 2,000 to about 25,000, and a weight average molecular weight ($M_w$) of, for example, from about 2,000 to about 100,000, in embodiments from about 3,000 to about 80,000, as determined by Gel Permeation Chromatography using polystyrene standards. The molecular weight distribution ($M_w/M_n$) of the crystalline resin may be, for example, from about 1.5 to about 6, in embodiments from about 2 to about 4.

Enzymes

As noted above, in embodiments the toner may be produced by enzymatic polymerization. The enzymes utilized thus serve as a catalyst in forming the crystalline polyester resins. Suitable enzymes to form polyesters include *Pseudomonas* family lipases, such as lipases from *Pseudomonas aeruginosa* (lipase PA), *Pseudomonas cepacia* (lipase PC), *Pseudomonas fluorescens* (lipase PF), as well as lipases from *Aspegillus niger* (lipase A), *Candida antarctica* (lipase CA or lipase B), *Candida cylindracea* (lipase CC), *Klebsiella oxytoca* (lipase K), *Mucor meihei* (lipase MM), cutinases such as the cutinase from *Humicola insolens*, combinations thereof, and the like.

In embodiments, the enzyme may be immobilized on a support member such as porous polymer beads, acrylic resins, cross-linked polystyrene, or any other suitable polymeric and/or ceramic supports within the purview of those skilled in the art.

The lipases or other enzymes may be obtained from the above organisms utilizing methods within the purview of those skilled in the art. In embodiments, the organisms may be grown in incubation vessels and fed with nutrients and sugars (e.g., glucose). By selecting the right growth and treatment conditions, lipases may be obtained from the organisms. In other embodiments, the lipases or other enzymes may be obtained from commercial sources, for example, Fluka BioChemika, Novozymes, and/or Sigma Aldrich.

The enzymes utilized to catalyze formation of the polyester resins are able to operate at temperatures of from about 10° C. to about 100° C., in embodiments from about 20° C. to about 90° C., in other embodiments from about 45° C. to about 75° C. One advantage of the immobilized enzymes that distinguishes them from other conventional catalysts is they can be separated from the product and re-used.

In embodiments, the amount of enzyme utilized to catalyze a reaction may be from about 0.1% by weight to about 10% by weight based on the starting materials used to generate the polyester resin, in embodiments from about 1% by weight to about 6% by weight based on the starting materials used to generate the polyester resin.

Reaction Conditions

The starting materials utilized to form the crystalline polyester resin, for example the lactones, cyclic anhydrides, and/or cyclic carbonates described above, may be combined with the above enzymes and a polyester may be formed by an enzymatic polymerization process. The enzymatic polymerization may be performed in the presence or absence of solvents.

In the enzymatic polymerization process, the reactants may be added to a suitable reactor, such as a mixing vessel. The appropriate amount of starting materials may be optionally dissolved in a solvent, a lipase based enzyme may be added to the solution, and a crystalline polyester formed which may then be used in the production of a toner. In other embodiments the starting materials may be combined with the lipase enzyme without solvent and a crystalline polyester formed. Other suitable reactors are within the purview of those skilled in the art and include, for example, those reactors disclosed in U.S. patent application Ser. No. 12/240,421, filed Sep. 29, 2008, the disclosure of which is hereby incorporated by references in its entirety.

Where utilized, suitable solvents include, but are not limited to, water and/or organic solvents including toluene, benzene, xylene, tetrahydrofuran, combinations thereof, and the like.

Where the starting materials are in solution, the starting materials may be at a concentration of from about 10% by weight to about 90% by weight, in embodiments from about 30% by weight to about 60% by weight.

As an example, the enzymatic polymerization of a lactone described above to form crystalline polyesters may proceed as follows:

Lactone

In embodiments, lactones having from about 2 to about 17 members may be catalyzed by the lipase enzyme to synthesize polylactones. Similarly, cyclic anhydrides and/or cyclic carbonates may be combined with enzymes to form polyesters. The resulting polyesters may be utilized to form copolymers of the present disclosure.

The time for the reaction may depend upon the type and amount of starting materials utilized, the amount of enzyme utilized, temperature, and the like. In embodiments, the reaction mixture may be mixed for from about 1 minute to about 72 hours, in embodiments from about 4 hours to about 24 hours, while keeping the temperature within the operational range of the lipase being used, in embodiments from about 10° C. to about 100° C., in embodiments from about 20° C. to about 90° C., in other embodiments from about 45° C. to about 75° C.

In embodiments, the reaction illustrated by formula (I) above may be performed directly in water.

In other embodiments a polyester emulsion may be directly produced by mixing one or more of the starting materials, enzyme, optional surfactant and water in a reactor to form an emulsion. More specifically, the starting materials and enzymes described above may be combined with water and one, two, or more surfactants. The surfactants may be selected from ionic surfactants and nonionic surfactants. Anionic surfactants and cationic surfactants are encompassed by the term "ionic surfactants." In embodiments, the surfactant may be utilized so that it is present in an amount of from about 0.01% to about 5% by weight of the polyester resin, for example from about 0.75% to about 4% by weight of the resin, in embodiments from about 1% to about 3% by weight of the resin.

Examples of nonionic surfactants that can be utilized include, for example, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, available from Rhone-Poulenc as IGEPAL CA210™, IGEPAL CA-520™, IGEPAL CA-720™, IGEPAL CO-890™, IGEPAL CO720™, IGEPAL CO290™, IGEPAL CA210™, ANTAROX 890™ and ANTAROX 897™. Other examples of suitable nonionic surfactants include a block copolymer of polyethylene oxide and polypropylene oxide, including those commercially available as SYNPERONIC PE/F, in embodiments SYNPERONIC PE/F 108. Yet other examples of suitable nonionic surfactants include ethoxylates of alkyl polyethylene glycol ethers based on the C10-Guerbet alcohol, including those commercially available as LUTENSOL® AT 50 from BASF.

Anionic surfactants which may be utilized include sulfates and sulfonates, sodium dodecylsulfate (SDS), sodium dodecylbenzene sulfonate, sodium dodecylnaphthalene sulfate, dialkyl benzenealkyl sulfates and sulfonates, acids such as abitic acid available from Aldrich, NEOGEN R™, NEOGEN SC™ obtained from Daiichi Kogyo Seiyaku, combinations thereof, and the like. Other suitable anionic surfactants include, in embodiments, DOWFAX™ 2A1, an alkyldiphenyloxide disulfonate from The Dow Chemical Company, and/or TAYCA POWER BN2060 from Tayca Corporation (Japan), which are branched sodium dodecyl benzene sulfonates. Combinations of these surfactants and any of the foregoing anionic surfactants may be utilized in embodiments.

Examples of the cationic surfactants, which are usually positively charged, include, for example, alkylbenzyl dimethyl ammonium chloride, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, $C_{12}$, $C_{15}$, $C_{17}$ trimethyl ammonium bromides, halide salts of quaternized polyoxyethylalkylamines, dodecylbenzyl triethyl ammonium chloride, MIRAPOL™ and ALKAQUAT™, available from Alkaril Chemical Company, SANIZOL™ (benzalkonium chloride), available from Kao Chemicals, and the like, and mixtures thereof.

In forming the emulsions, the starting materials, enzyme, surfactant, and water may be combined utilizing any means within the purview of those skilled in the art. In embodiments, the reaction mixture may be mixed for from about 1 minute to about 72 hours, in embodiments from about 4 hours to about 24 hours, while keeping the temperature within the operational range of the lipase being used, in embodiments from about 10° C. to about 100° C., in embodiments from about 20° C. to about 90° C., in other embodiments from about 45° C. to about 75° C.

In embodiments, a coalescence inhibitor may be added to the emulsion to aid in the formation of miniemulsions, for example, minimize the formation of large particles in the emulsion and to enhance emulsion stability by preventing coalescence and Ostwald ripening. Suitable coalescence inhibitors may include one or more of the following: hydrocarbons, including alkanes or cycloalkanes, in embodiments alkanes or cycloalkanes having at least 12 carbon atoms (such as hexadecane and/or octadecane); long chain alcohols (such as hexadecanol and/or octadecanol); halogenated hydrocarbons, organosilicon compounds, long-chain esters, oils, including vegetable oils (such as olive oil), hydrophobic dye molecules, capped isocyanates, oligomeric and/or polymeric products of polymerization, polycondensation or polyaddition, such as polymeric co-stabilizers, combinations thereof, and the like. The amount of coalescence inhibitor added to the reaction mixture may be from about 0.01% weight to about 40% weight, in embodiments from about 0.1% weight to about 10% weight. The weights of hydrophobic co-stabilizer used herein are calculated relative to the total weight of the mixture prepared in the process of the present disclosure.

Those skilled in the art will recognize that optimization of reaction conditions, temperature, and enzyme loading can be varied to generate polyesters of various molecular weights, and that structurally related starting materials may be polymerized using comparable techniques.

Resins thus produced may include particles possessing a size of from about 20 nanometers to about 1000 nanometers, in embodiments from about 50 nanometers to about 250 nanometers. The resins thus produced may have a glass transition temperature (Tg) of from about −100° C. to about 200° C., in embodiments from about −50° C. to about 20° C. Resins thus produced may have a melting point (Tm) of from about 45° C. to about 100° C., in embodiments form about 55° C. to about 95° C. The molecular weight of the polyester may be from about 1,000 to about 50,000, in embodiments from about 3,000 to about 20,000.

In accordance with the present disclosure, resins may be produced with the desired melting point from mixtures of pentadecalactone and pentadecenlactone according to the following formula:

$$Tm = 92.6 − (32.7)x,$$

where Tm is the melting point of the resulting resin in degrees Celsius and x is the mole fraction of pentadecenlactone present in the monomer mixture. As one skilled in the art would appreciate, there may be slight deviations (of a few degrees, either way) from the straight line implied by this equation.

As noted above, enzymatic polymerization may be used in accordance with the present disclosure to directly form a crystalline polyester latex in water. During the polymerization process, water may be one of the byproducts as a result of dehydration. Thus, while a conventional polymerization reaction of the above-identified monomers may be difficult in water due to the law of mass action, enzymatic polymerization in water may circumvent this problem due to a reduction in the activation barrier for catalysis by the lipase enzyme. The lipase enzymes may remove water molecules from the reactants and create an environment similar to the gas phase for the reactants. It is also envisioned that the lipase enzyme may remove water molecules from the reactants and substitute the removed water molecules for its active site, which is adapted for electrostatic stabilization of ionic transition states and solvates these states more effectively than water.

The weight of the resulting polymers may depend, on the starting materials, reaction conditions, and the lipase enzyme being used. Higher temperatures, in embodiments about 60° C. or above, and longer reaction times of about forty eight (48) or more hours, may yield polymers with higher molecular weights.

In embodiments, the final water-borne polyester emulsion may be utilized to form toner particles. In embodiments, if the particle size of the polyester in the emulsion is too large, the emulsion may be subjected to homogenizing or sonication to further disperse the nanoparticles and break apart any agglomerates or loosely bound particles. Where utilized, a homogenizer, (that is, a high shear device), may operate at a rate of from about 6,000 rpm to about 10,000 rpm, in embodiments from about 7,000 rpm to about 9,750 rpm, for a period of time of from about 0.5 minutes to about 60 minutes, in embodiments from about 5 minute to about 30 minutes.

Utilizing the methods of the present disclosure, one can fine-tune the melting properties, for example the melting point, of crystalline polyesters produced by the enzymatic ring-opening synthesis of large-ring lactones, cyclic anhydrides, cyclic carbonates, and the like. The enzymatic polymerization process uses lower temperatures and shorter reaction times than traditional polycondensation. The range of available crystalline polyesters is greatly expanded, which in turn removes some of the design restrictions on amorphous-crystalline resin combinations for a low-melt polyester toner and provides a greater range of options to improve toner properties. The present disclosure allows one to form a crystalline polyester with a specific melting point, independently of molecular weight, by fine adjustment of the polymer composition, that is, by adjusting the amounts of the monomers utilized to form a copolymer in accordance with the present disclosure. In embodiments, the relationship of polymer melting point to co-polymer composition may be nearly linear in nature.

Toner

The resin described above may be utilized to form toner compositions. As noted above, the crystalline copolymer (polyester) produced may be combined with an amorphous resin to form toner particles. In embodiments, the amorphous resin may be a polyester resin formed by reacting a diol with a diacid in the presence of an optional catalyst. Examples of diacid or diesters selected for the preparation of amorphous polyesters include dicarboxylic acids or diesters such as terephthalic acid, phthalic acid, isophthalic acid, fumaric acid, maleic acid, maleic anhydride, succinic acid, malonic acid, itaconic acid, 2-methylitaconic acid, 2-ethyl succinic acid, succinic anhydride, dodecylsuccinic acid, 2-methyladipic acid, dodecylsuccinic anhydride, glutaric acid, glutaric anhydride, adipic acid, pimelic acid, suberic acid, azelaic acid, sebacic acid, dodecanedioic acid, dimethyl terephthalate, diethyl terephthalate, dimethylisophthalate, diethylisophthalate, dimethylphthalate, phthalic anhydride, diethylphthalate, dimethylsuccinate, dimethylfumarate, dimethylmaleate, dimethylglutarate, dimethyladipate, dimethyl dodecylsuccinate, and combinations thereof. The organic diacid or diester may be present, for example, in an amount from about 40 to about 60 mole percent of the resin, in embodiments from about 42 to about 55 mole percent of the resin, in embodiments from about 45 to about 53 mole percent of the resin.

Examples of diols utilized in generating the amorphous polyester include 1,2-propanediol, 1,3-propanediol, 1,2-butanediol, 1,3-butanediol, 1,4-butanediol, pentanediol, hexanediol, 2,2-dimethylpropanediol, 2,2,3-trimethylhexanediol, heptanediol, dodecanediol, bis(hydroxyethyl)-bisphenol A, bis(2-hydroxypropyl)-bisphenol A, 1,4-cyclohexanedimethanol, 1,3-cyclohexanedimethanol, xylenedimethanol, cyclohexanediol, diethylene glycol, bis(2-hydroxyethyl) oxide, dipropylene glycol, dibutylene, and combinations thereof. The amount of organic diol selected can vary, and may be present, for example, in an amount from about 40 to about 60 mole percent of the resin, in embodiments from about 42 to about 55 mole percent of the resin, in embodiments from about 45 to about 53 mole percent of the resin.

Polycondensation catalysts which may be utilized for either the crystalline or amorphous polyesters include tetraalkyl titanates, dialkyltin oxides such as dibutyltin oxide, tetraalkyltins such as dibutyltin dilaurate, and dialkyltin oxide hydroxides such as butyltin oxide hydroxide, aluminum alkoxides, alkyl zinc, dialkyl zinc, zinc oxide, stannous oxide, or combinations thereof. Other catalysts which may be used include, for example, non-metal catalysts such as akyl benzene sulfonates, alkyl sulfonates, and combinations thereof. Any of the above catalysts may be utilized in amounts of, for example, from about 0.01 mole percent to about 5 mole percent based on the starting diacid or diester used to generate the polyester resin.

In embodiments, suitable amorphous resins include polyesters, polyamides, polyimides, polyolefins, polyethylene, polybutylene, polyisobutyrate, ethylene-propylene copolymers, ethylene-vinyl acetate copolymers, polypropylene, combinations thereof, and the like. Examples of amorphous resins which may be utilized include poly(styrene-acrylate) resins, crosslinked, for example, from about 10 percent to about 70 percent, poly(styrene-acrylate) resins, poly(styrene-methacrylate) resins, crosslinked poly(styrene-methacrylate) resins, poly(styrene-butadiene) resins, crosslinked poly(styrene-butadiene) resins, alkali sulfonated-polyester resins, branched alkali sulfonated-polyester resins, alkali sulfonated-polyimide resins, branched alkali sulfonated-polyimide resins, alkali sulfonated poly(styrene-acrylate) resins, crosslinked alkali sulfonated poly(styrene-acrylate) resins, poly(styrene-methacrylate) resins, crosslinked alkali sulfonated-poly(styrene-methacrylate) resins, alkali sulfonated-poly(styrene-butadiene) resins, and crosslinked alkali sulfonated poly(styrene-butadiene) resins. Alkali sulfonated polyester resins may be useful in embodiments, such as the metal or alkali salts of copoly(ethylene-terephthalate)-copoly(ethylene-5-sulfo-isophthalate), copoly(propylene-terephthalate)-copoly(propylene-5-sulfo-isophthalate), copoly(diethylene-terephthalate)-copoly(diethylene-5-sulfo-isophthalate), copoly(propylene-diethylene-terephthalate)-copoly(propylene-diethylene-5-sulfoisophthalate), copoly(propylene-butylene-terephthalate)-copoly(propylene-butylene-5-sulfo-isophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), and copoly(ethoxylated bisphenol-A-maleate)-copoly(ethoxylated bisphenol-A-5-sulfo-isophthalate), and wherein the alkali metal is, for example, a sodium, lithium or potassium ion.

Examples of other suitable latex resins or polymers which may be utilized include, but are not limited to, poly(styrene-butadiene), poly(methylstyrene-butadiene), poly(methyl methacrylate-butadiene), poly(ethyl methacrylate-butadiene), poly(propyl methacrylate-butadiene), poly(butyl methacrylate-butadiene), poly(methyl acrylate-butadiene), poly(ethyl acrylate-butadiene), poly(propyl acrylate-butadiene), poly(butyl acrylate-butadiene), poly(styrene-isoprene), poly(methylstyrene-isoprene), poly(methyl methacrylate-isoprene), poly(ethyl methacrylate-isoprene), poly(propyl methacrylate-isoprene), poly(butyl methacrylate-isoprene), poly(methyl acrylate-isoprene), poly(ethyl acrylate-isoprene), poly(propyl acrylate-isoprene), poly(butyl acrylate-isoprene); poly(styrene-propyl acrylate), poly(styrene-butyl acrylate), poly(styrene-butadiene-acrylic acid), poly(styrene-butadiene-methacrylic acid), poly(styrene-butadiene-acrylonitrile-acrylic acid), polystyrene-butyl acrylate-acrylic acid), poly(styrene-butyl acrylate-methacrylic acid), poly(styrene-butyl acrylate-acrylonitrile), and poly(styrene-butyl acrylate-acrylonitrile-acrylic acid), and combinations thereof. The polymers may be block, random, or alternating copolymers.

In embodiments, an unsaturated polyester resin may be utilized as a latex resin. Examples of such resins include those disclosed in U.S. Pat. No. 6,063,827, the disclosure of which is hereby incorporated by reference in its entirety. Exemplary unsaturated polyester resins include, but are not limited to, poly(propoxylated bisphenol co-fumarate), poly(ethoxylated bisphenol co-fumarate), poly(butyloxylated bisphenol co-fumarate), poly(co-propoxylated bisphenol co-ethoxylated bisphenol co-fumarate), poly(1,2-propylene fumarate), poly(propoxylated bisphenol co-maleate), poly(ethoxylated bisphenol co-maleate), poly(butyloxylated bisphenol co-maleate), poly(co-propoxylated bisphenol co-ethoxylated bisphenol co-maleate), poly(1,2-propylene maleate), poly(propoxylated bisphenol co-itaconate), poly(ethoxylated bisphenol co-itaconate), poly(butyloxylated bisphenol co-itaconate), poly(co-propoxylated bisphenol co-ethoxylated bisphenol co-itaconate), poly(1,2-propylene itaconate), and combinations thereof.

In embodiments, a suitable amorphous polyester resin may be a poly(propoxylated bisphenol A co-fumarate) resin having the following formula (I):

(I)

wherein m may be from about 5 to about 1000.

An example of a linear propoxylated bisphenol A fumarate resin which may be utilized as a latex resin is available under the trade name SPAMII from Resana S/A Industrias Quimicas, Sao Paulo, Brazil. Other propoxylated bisphenol A fumarate resins that may be utilized and are commercially available include GTUF and FPESL-2 from Kao Corporation, Japan, and EM181635 from Reichhold, Research Triangle Park, N.C. and the like.

In embodiments combinations of amorphous resins having low molecular weights and high molecular weights may be utilized. A low molecular weight amorphous resin may have a weight average molecular weight (Mw) of from about 15 kg/mol to about 45 kg/mol, in embodiments from about 20 kg/mol to about 40 kg/mol, and a high molecular weight resin may have a weight average molecular weight (Mw) of from about 25 kg/mol to about 55 kg/mol, in embodiments from about 35 kg/mol to about 50 kg/mol.

Toner compositions of the present disclosure may also include optional colorants, waxes, and other additives. Toners may be formed utilizing any method within the purview of those skilled in the art.

The crystalline resin may be present, for example, in an amount of from about 1 to about 30 percent by weight of the toner components, in embodiments from about 5 to about 20 percent by weight of the toner components. The amorphous resin may be present, for example, in an amount of from about 5 to about 60 percent by weight of the toner components, in embodiments from about 20 to about 50 percent by weight of the toner components.

Surfactants

In embodiments, colorants, waxes, and other additives utilized to form toner compositions may be in dispersions including surfactants. Moreover, toner particles may be formed by emulsion aggregation methods where the resin and other components of the toner are placed in one or more surfactants, an emulsion is formed, toner particles are aggregated, coalesced, optionally washed and dried, and recovered.

One, two, or more surfactants may be utilized. The surfactants may be selected from ionic surfactants and nonionic surfactants. Anionic surfactants and cationic surfactants are encompassed by the term "ionic surfactants." In embodiments, the surfactant may be utilized so that it is present in an amount of from about 0.01% to about 5% by weight of the toner composition, for example from about 0.75% to about 4% by weight of the toner composition, in embodiments from about 1% to about 3% by weight of the toner composition.

Examples of nonionic surfactants that can be utilized include, for example, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, available from Rhone-Poulenc as IGEPAL CA210™, IGEPAL CA-520™, IGEPAL CA-720™, IGEPAL CO-890™, IGEPAL CO720™, IGEPAL CO290™, IGEPAL CA210™, ANTAROX 890™ and ANTAROX 897™. Other examples of suitable nonionic surfactants include a block copolymer of polyethylene oxide and polypropylene oxide, including those commercially available as SYNPERONIC PE/F, in embodiments SYNPERONIC PE/F 108.

Anionic surfactants which may be utilized include sulfates and sulfonates, sodium dodecylsulfate (SDS), sodium dodecylbenzene sulfonate, sodium dodecylnaphthalene sulfate, dialkyl benzenealkyl sulfates and sulfonates, acids such as abitic acid available from Aldrich, NEOGEN R™, NEOGEN SC™ obtained from Daiichi Kogyo Seiyaku, combinations thereof, and the like. Other suitable anionic surfactants include, in embodiments, DOWFAX™ 2A1, an alkyldiphenyloxide disulfonate from The Dow Chemical Company, and/or TAYCA POWER BN2060 from Tayca Corporation (Japan), which are branched sodium dodecyl benzene sulfonates. Combinations of these surfactants and any of the foregoing anionic surfactants may be utilized in embodiments.

Examples of the cationic surfactants, which are usually positively charged, include, for example, alkylbenzyl dimethyl ammonium chloride, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, $C_{12}$, $C_{15}$, $C_{17}$ trimethyl ammonium bromides, halide salts of quatemized polyoxyethylalkylamines, dodecylbenzyl triethyl ammonium chloride, MIRAPOL™ and ALKAQUAT™, available from Alkaril Chemical Company, SANIZOL™ (benzalkonium chloride), available from Kao Chemicals, and the like, and mixtures thereof.

Colorants

As the colorant to be added, various known suitable colorants, such as dyes, pigments, mixtures of dyes, mixtures of pigments, mixtures of dyes and pigments, and the like, may be included in the toner. The colorant may be included in the toner in an amount of, for example, about 0.1 to about 35 percent by weight of the toner, or from about 1 to about 15 weight percent of the toner, or from about 3 to about 10 percent by weight of the toner.

As examples of suitable colorants, mention may be made of carbon black like REGAL 330®; magnetites, such as Mobay magnetites MO8029™, MO8060™; Columbian magnetites; MAPICO BLACKS™ and surface treated magnetites; Pfizer magnetites CB4799™, CB5300™, CB5600™, MCX6369™; Bayer magnetites, BAYFERROX 8600™, 8610™; Northern Pigments magnetites, NP604™, NP608™; Magnox magnetites TMB-100™, or TMB-104™; and the like. As colored pigments, there can be selected cyan, magenta, yellow, red, green, brown, blue or mixtures thereof. Generally, cyan, magenta, or yellow pigments or dyes, or mixtures thereof, are used. The pigment or pigments are generally used as water based pigment dispersions.

Specific examples of pigments include SUNSPERSE 6000, FLEXIVERSE and AQUATONE water based pigment dispersions from SUN Chemicals, HELIOGEN BLUE L6900™, D6840™, D7080™, D7020™, PYLAM OIL BLUE™, PYLAM OIL YELLOW™, PIGMENT BLUE 1™ available from Paul Uhlich & Company, Inc., PIGMENT VIOLET 1™, PIGMENT RED 48™, LEMON CHROME YELLOW DCC 1026™, E.D. TOLUIDINE RED™ and BON RED C™ available from Dominion Color Corporation, Ltd., Toronto, Ontario, NOVAPERM YELLOW FGL™, HOSTAPERM PINK E™ from Hoechst, and CINQUASIA MAGENTA™ available from E.I. DuPont de Nemours & Company, and the like. Generally, colorants that can be selected are black, cyan, magenta, or yellow, and mixtures thereof. Examples of magentas are 2,9-dimethyl-substituted quinacridone and anthraquinone dye identified in the Color Index as CI 60710, CI Dispersed Red 15, diazo dye identified in the Color Index as CI 26050, CI Solvent Red 19, and the like. Illustrative examples of cyans include copper tetra(octadecyl sulfonamido) phthalocyanine, x-copper phthalocyanine pigment listed in the Color Index as CI 74160, CI Pigment Blue, Pigment Blue 15:3, and Anthrathrene Blue, identified in the Color Index as CI 69810, Special Blue X-2137, and the like. Illustrative examples of yellows are diarylide yellow 3,3-dichlorobenzidene acetoacetanilides, a monoazo pigment identified in the Color Index as CI 12700, CI Solvent Yellow 16, a nitrophenyl amine sulfonamide identified in the Color Index as Foron Yellow SE/GLN, CI Dispersed Yellow 33 2,5-dimethoxy-4-sulfonanilide phenylazo- 4'-chloro-2,5-dimethoxy acetoacetanilide, and Permanent Yellow FGL. Colored magnetites, such as mixtures of MAPICO BLACK™, and cyan components may also be selected as colorants. Other known colorants can be selected, such as Levanyl Black A-SF (Miles, Bayer) and Sunsperse Carbon Black LHD 9303 (Sun Chemicals), and colored dyes such as Neopen Blue (BASF), Sudan Blue OS (BASF), PV Fast Blue B2G01 (American Hoechst), Sunsperse Blue BHD 6000 (Sun Chemicals), Irgalite Blue BCA (Ciba-Geigy), Paliogen Blue 6470 (BASF), Sudan III (Matheson, Coleman, Bell), Sudan II (Matheson, Coleman, Bell), Sudan IV (Matheson, Coleman, Bell), Sudan Orange G (Aldrich), Sudan Orange 220 (BASF), Paliogen Orange 3040 (BASF), Ortho Orange OR 2673 (Paul Uhlich), Paliogen Yellow 152, 1560 (BASF), Lithol Fast Yellow 0991K (BASF), Paliotol Yellow 1840 (BASF), Neopen Yellow (BASF), Novoperm Yellow FG 1 (Hoechst), Permanent Yellow YE 0305 (Paul Uhlich), Lumogen Yellow D0790 (BASF), Sunsperse Yellow YHD 6001 (Sun Chemicals), Suco-Gelb L1250 (BASF), Suco-Yellow D1355 (BASF), Hostaperm Pink E (American Hoechst), Fanal Pink D4830 (BASF), Cinquasia Magenta (DuPont), Lithol Scarlet D3700 (BASF), Toluidine Red (Aldrich), Scarlet for Thermoplast NSD PS PA (Ugine Kuhlmann of Canada), E.D. Toluidine Red (Aldrich), Lithol Rubine Toner (Paul Uhlich), Lithol Scarlet 4440 (BASF), Bon Red C (Dominion Color Company), Royal Brilliant Red RD-8192 (Paul Uhlich), Oracet Pink RF (Ciba-Geigy), Paliogen Red 3871K (BASF), Paliogen Red 3340 (BASF), Lithol Fast Scarlet L4300 (BASF), combinations of the foregoing, and the like.

Wax

Optionally, a wax may also be combined with the resin and a colorant in forming toner particles. When included, the wax may be present in an amount of, for example, from about 1 weight percent to about 25 weight percent of the toner particles, in embodiments from about 5 weight percent to about 20 weight percent of the toner particles.

Waxes that may be selected include waxes having, for example, a weight average molecular weight of from about 500 to about 20,000, in embodiments from about 1,000 to about 10,000. Waxes that may be used include, for example, polyolefins such as polyethylene, polypropylene, and polybutene waxes such as commercially available from Allied Chemical and Petrolite Corporation, for example POLYWAX™ polyethylene waxes from Baker Petrolite, wax emulsions available from Michaelman, Inc. and the Daniels Products Company, EPOLENE N-15 ™ commercially available from Eastman Chemical Products, Inc., and VISCOL 55-P™, a low weight average molecular weight polypropylene available from Sanyo Kasei K. K.; plant-based waxes, such as carnauba wax, rice wax, candelilla wax, sumacs wax, and jojoba oil; animal-based waxes, such as beeswax; mineral-based waxes and petroleum-based waxes, such as montan wax, ozokerite, ceresin, paraffin wax, microcrystalline wax, and Fischer-Tropsch wax; ester waxes obtained from higher fatty acid and higher alcohol, such as stearyl stearate and behenyl behenate; ester waxes obtained from higher fatty acid and monovalent or multivalent lower alcohol, such as butyl stearate, propyl oleate, glyceride monostearate, glyceride distearate, and pentaerythritol tetra behenate; ester waxes obtained from higher fatty acid and multivalent alcohol multimers, such as diethyleneglycol monostearate, dipropyleneglycol distearate, diglyceryl distearate, and triglyceryl tetrastearate; sorbitan higher fatty acid ester waxes, such as sorbitan monostearate, and cholesteryl higher fatty acid ester waxes, such as cholesteryl stearate. Examples of functionalized waxes that may be used include, for example, amines, amides, for example AQUA SUPERSLIP 6550™, SUPERSLIP 6530™ available from Micro Powder Inc., fluorinated waxes, for example POLYFLUO 190™, POLYFLUO 200™, POLYSILK 19™, POLYSILK 14™ available from Micro Powder Inc., mixed fluorinated, amide waxes, for example MICROSPERSION 1™ also available from Micro Powder Inc., imides, esters, quaternary amines, carboxylic acids or acrylic polymer emulsion, for example JONCRYL 74™, 89™, 130™, 537™, and 538™, all available from SC Johnson Wax, and chlorinated polypropylenes and polyethylenes available from Allied Chemical and Petrolite Corporation and SC Johnson wax. Mixtures and combinations of the foregoing waxes may also be used in embodiments. Waxes may be included as, for example, fuser roll release agents.

Toner Preparation

The toner particles may be prepared by any method within the purview of one skilled in the art. Although embodiments relating to toner particle production are described below with respect to emulsion-aggregation processes, any suitable method of preparing toner particles may be used, including chemical processes, such as suspension and encapsulation processes disclosed in U.S. Pat. Nos. 5,290,654 and 5,302,486, the disclosures of each of which are hereby incorporated by reference in their entirety. In embodiments, toner compositions and toner particles may be prepared by aggregation and coalescence processes in which small-size resin particles are aggregated to the appropriate toner particle size and then coalesced to achieve the final toner particle shape and morphology.

In embodiments, toner compositions may be prepared by emulsion-aggregation processes, such as a process that includes aggregating a mixture of an optional colorant, an optional wax and any other desired or required additives, and emulsions including the resins described above, optionally in surfactants as described above, and then coalescing the aggregate mixture. A mixture may be prepared by adding a colorant and optionally a wax or other materials, which may also be optionally in a dispersion(s) including a surfactant, to the emulsion, which may be a mixture of two or more emulsions containing the resin. The pH of the resulting mixture may be adjusted by an acid such as, for example, acetic acid, nitric acid or the like. In embodiments, the pH of the mixture may be adjusted to from about 4 to about 5. Additionally, in embodiments, the mixture may be homogenized. If the mixture is homogenized, homogenization may be accomplished by mixing at about 600 to about 4,000 revolutions per minute. Homogenization may be accomplished by any suitable means, including, for example, an IKA ULTRA TURRAX T50 probe homogenizer.

Following the preparation of the above mixture, an aggregating agent may be added to the mixture. Any suitable aggregating agent may be utilized to form a toner. Suitable aggregating agents include, for example, aqueous solutions of a divalent cation or a multivalent cation material. The aggregating agent may be, for example, polyaluminum halides such as polyaluminum chloride (PAC), or the corresponding bromide, fluoride, or iodide, polyaluminum silicates such as polyaluminum sulfosilicate (PASS), and water soluble metal salts including aluminum chloride, aluminum nitrite, aluminum sulfate, potassium aluminum sulfate, calcium acetate, calcium chloride, calcium nitrite, calcium oxylate, calcium sulfate, magnesium acetate, magnesium nitrate, magnesium sulfate, zinc acetate, zinc nitrate, zinc sulfate, zinc chloride, zinc bromide, magnesium bromide, copper chloride, copper sulfate, and combinations thereof. In embodiments, the aggregating agent may be added to the mixture at a temperature that is below the glass transition temperature (Tg) of the resin.

The aggregating agent may be added to the mixture utilized to form a toner in an amount of, for example, from about 0.1% to about 8% by weight, in embodiments from about 0.2% to about 5% by weight, in other embodiments from about 0.5% to about 5% by weight, of the resin in the mixture. This provides a sufficient amount of agent for aggregation.

In order to control aggregation and coalescence of the particles, in embodiments the aggregating agent may be metered into the mixture over time. For example, the agent may be metered into the mixture over a period of from about 5 to about 240 minutes, in embodiments from about 30 to about 200 minutes, although more or less time may be used as desired or required. The addition of the agent may also be done while the mixture is maintained under stirred conditions, in embodiments from about 50 rpm to about 1,000 rpm, in other embodiments from about 100 rpm to about 500 rpm, and at a temperature that is below the glass transition temperature of the resin as discussed above, in embodiments from about 30° C. to about 90° C., in embodiments from about 35° C. to about 70° C.

The particles may be permitted to aggregate and/or coalesce until a predetermined desired particle size is obtained. A predetermined desired size refers to the desired particle size to be obtained as determined prior to formation, and the particle size being monitored during the growth process until such particle size is reached. Samples may be taken during the growth process and analyzed, for example with a Coulter Counter, for average particle size. The aggregation/coalescence thus may proceed by maintaining the elevated temperature, or slowly raising the temperature to, for example, from about 40° C. to about 100° C., and holding the mixture at this temperature for a time from about 0.5 hours to about 6 hours, in embodiments from about hour 1 to about 5 hours, while maintaining stirring, to provide the aggregated particles. Once the predetermined desired particle size is reached, then the growth process is halted. In embodiments, the predetermined desired particle size is within the toner particle size ranges mentioned above.

The growth and shaping of the particles following addition of the aggregation agent may be accomplished under any suitable conditions. For example, the growth and shaping may be conducted under conditions in which aggregation occurs separate from coalescence. For separate aggregation and coalescence stages, the aggregation process may be conducted under shearing conditions at an elevated temperature, for example of from about 40° C. to about 90° C., in embodiments from about 45° C. to about 80° C., which may be below the glass transition temperature of the resin as discussed above.

Following aggregation to the desired particle size, the particles may then be coalesced to the desired final shape, the coalescence being achieved by, for example, heating the mixture to a temperature of from about 65° C. to about 105° C., in embodiments from about 70° C. to about 95° C., which may be at or above the glass transition temperature of the resin, and/or increasing the stirring, for example to from about 400 rpm to about 1,000 rpm, in embodiments from about 500 rpm to about 800 rpm. Higher or lower temperatures may be used, it being understood that the temperature is a function of the resins used for the binder. Coalescence may be accomplished over a period of from about 0.1 to about 9 hours, in embodiments from about 0.5 to about 4 hours.

After aggregation and/or coalescence, the mixture may be cooled to room temperature, such as from about 20° C. to about 25° C. The cooling may be rapid or slow, as desired. A suitable cooling method may include introducing cold water to a jacket around the reactor. After cooling, the toner particles may be optionally washed with water, and then dried. Drying may be accomplished by any suitable method for drying including, for example, freeze-drying.

Finishing

After aggregation, but prior to coalescence, once the desired final size of the toner particles is achieved, the pH of the mixture may be adjusted with a base to a value of from about 3 to about 10, and in embodiments from about 5 to about 9. The adjustment of the pH may be utilized to freeze, that is to stop, toner growth. The base utilized to stop toner growth may include any suitable base such as, for example, alkali metal hydroxides such as, for example, sodium hydroxide, potassium hydroxide, ammonium hydroxide, combinations thereof, and the like. In embodiments, ethylene diamine tetraacetic acid (EDTA) may be added to help adjust the pH to the desired values noted above.

Shell Resin

In embodiments, after aggregation, but prior to coalescence, a shell may be applied to the aggregated particles. Any resin described above may be applied as a shell. In embodiments an amorphous resin may be applied as the shell. The shell may have a thickness of from about 50 nm to about 2 microns, in embodiments from about 200 nm to about 1 micron.

The shell resin may be applied to the aggregated particles by any method within the purview of those skilled in the art. In embodiments, the shell resin may be in an emulsion including any surfactant described above. The aggregated particles described above may be combined with said emulsion so that the shell resin forms a shell over the formed aggregates.

Additives

In embodiments, the toner particles may also contain other optional additives, as desired or required. For example, the toner may include positive or negative charge control agents, for example in an amount of from about 0.1 to about 10 percent by weight of the toner, in embodiments from about 1 to about 3 percent by weight of the toner. Examples of suitable charge control agents include quaternary ammonium compounds inclusive of alkyl pyridinium halides; bisulfates; alkyl pyridinium compounds, including those disclosed in U.S. Pat. No. 4,298,672, the disclosure of which is hereby incorporated by reference in its entirety; organic sulfate and sulfonate compositions, including those disclosed in U.S. Pat. No. 4,338,390, the disclosure of which is hereby incorporated by reference in its entirety; cetyl pyridinium tetrafluoroborates; distearyl dimethyl ammonium methyl sulfate; aluminum salts such as BONTRON E84™ or E88™ (Hodogaya Chemical); combinations thereof, and the like. Such charge control agents may be applied simultaneously with the shell resin described above or after application of the shell resin.

There can also be blended with the toner particles external additive particles including flow aid additives, which additives may be present on the surface of the toner particles. Examples of these additives include metal oxides such as titanium oxide, silicon oxide, tin oxide, mixtures thereof, and the like; colloidal and amorphous silicas, such as AEROSIL®, metal salts and metal salts of fatty acids inclusive of zinc stearate, aluminum oxides, cerium oxides, and mixtures thereof. Each of these external additives may be present in an amount of from about 0.1 percent by weight to about 5 percent by weight of the toner, in embodiments of from about 0.25 percent by weight to about 3 percent by weight of the toner. Suitable additives include those disclosed in U.S. Pat. Nos. 3,590,000, 3,800,588, and 6,214,507, the disclosures of each of which are hereby incorporated by reference in their entirety. Again, these additives may be applied simultaneously with the shell resin described above or after application of the shell resin.

In embodiments, toners of the present disclosure may be utilized as low-melt polyester toners. In embodiments, the dry toner particles, exclusive of external surface additives, may have the following characteristics:

(1) Volume average diameter (also referred to as "volume average particle diameter") of from about 3 microns to about 25 microns, in embodiments from about 4 microns to about 15 microns, in other embodiments from about 5 microns to about 12 microns.

(2) Number Average Geometric Size Distribution (GSDn) and/or Volume Average Geometric Size Distribution (GSDv) of from about 1.05 to about 1.55, in embodiments from about 1.1 to about 1.4.

(3) Circularity of from about 0.9 to about 0.99, in embodiments from about 0.92 to about 0.98 (measured with, for example, a Sysmex FPIA 2100 analyzer).

The characteristics of the toner particles may be determined by any suitable technique and apparatus. Volume average particle diameter $D_{50v}$, GSDv, and GSDn may be measured by means of a measuring instrument such as a Beckman Coulter Multisizer 3, operated in accordance with the manufacturer's instructions. Representative sampling may occur as follows: a small amount of toner sample, about 1 gram, may be obtained and filtered through a 25 micrometer screen, then put in isotonic solution to obtain a concentration of about 10%, with the sample then run in a Beckman Coulter Multisizer 3.

Toners produced in accordance with the present disclosure may possess excellent charging characteristics when exposed to extreme relative humidity (RH) conditions. The low-humidity zone (C zone) is about 10° C./15% RH, while the high humidity zone (A zone) is about 28° C./85% RH. Toners of the present disclosure may also possess a parent toner charge per mass ratio (Q/M) of from about −3 µC/g to about −35 µC/g, and a final toner charging after surface additive blending of from −5 µC/g to about −50 µC/g.

In accordance with the present disclosure, the charging of the toner particles may be enhanced, so less surface additives may be required, and the final toner charging may thus be higher to meet machine charging requirements.

Uses

The enzymatic polymerization synthesis according to the present disclosure may be used to prepare resins for use in subsequent synthesis of emulsion aggregation toners either in the presence or absence of solvents. Crystalline or amorphous polyester resins with a range of thermodynamic and chemical properties may be produced. The disclosed enzymatic synthesis also provides for reduced reaction times and energy costs, since lipase based synthesis occurs at temperatures from about 10° C. to about 100° C., in embodiments for a period of time as short as about four hours, whereas processes with conventional catalysts may require temperatures above about 150° C. and may take at least eight or more hours.

As noted above, in embodiments lipase enzymes may be used to catalyze ring-opening polymerization of lactones, even large-ring lactones, such as pentadecalactone and hexadecenlactone, to obtain corresponding polyesters thereof. Large-ring lactones may be resistant to traditional chemical polymerization processes due to low ring strain of these compounds. Enzymatic polymerization may thus produce polyester structures which are not available through conventional lactone polymerization processes. More specifically, polymerization of pentadecalactone may produce a crystalline polymer with a melting point of at least 79° C., depending on molecular weight, and polymerization of hexadecenlactone may produce a polymer having a much lower melting point of 57° C. It is envisioned that co-polymerization of these monomers, as well as other lactones, such as pentadecenlactone, caprolactone, derivatives of caprolactone and similar compounds, may be used to produce polymers of any suitable crystallinity and melting/glass transition temperatures.

In addition, lactones suitable for enzymatic polymerization are readily available, making the starting material relatively inexpensive since the large-ring lactones are widely used in other industries, for example fragrance, food additives, and the like.

Further, the lipase enzymes are reusable, thereby reducing the costs associated with their use. Thus, the enzymatic polymerization processes of the present disclosure, including the formation of water-borne polyester emulsions described above, are environmentally friendly by reducing the energy required for production, by reducing the use of solvents by avoiding phase inversion and/or solvent flashing steps, are reusable, and renewable (enzymes are grown in an engineered bacterial culture). The enzymatic polymerization processes of the present disclosure also provide the ability to synthesize a wider range of polymer structures than traditional methods.

Developers

The toner particles may be formulated into a developer composition. The toner particles may be mixed with carrier particles to achieve a two-component developer composition. The toner concentration in the developer may be from about 1% to about 25% by weight of the total weight of the developer, in embodiments from about 2% to about 15% by weight of the total weight of the developer.

Carriers

Examples of carrier particles that can be utilized for mixing with the toner include those particles that are capable of triboelectrically obtaining a charge of opposite polarity to that of the toner particles. Illustrative examples of suitable carrier particles include granular zircon, granular silicon, glass, steel, nickel, ferrites, iron ferrites, silicon dioxide, and the like. Other carriers include those disclosed in U.S. Pat. Nos. 3,847,604, 4,937,166, and 4,935,326.

The selected carrier particles can be used with or without a coating. In embodiments, the carrier particles may include a core with a coating thereover which may be formed from a mixture of polymers that are not in close proximity thereto in the triboelectric series. The coating may include fluoropolymers, such as polyvinylidene fluoride resins, terpolymers of styrene, methyl methacrylate, and/or silanes, such as triethoxy silane, tetrafluoroethylenes, other known coatings and the like. For example, coatings containing polyvinylidenefluoride, available, for example, as KYNAR 301F™, and/or polymethylmethacrylate, for example having a weight average molecular weight of about 300,000 to about 350,000, such as commercially available from Soken, may be used. In embodiments, polyvinylidenefluoride and polymethylmethacrylate (PMMA) may be mixed in proportions of from about 30 to about 70 weight % to about 70 to about 30 weight %, in embodiments from about 40 to about 60 weight % to about 60 to about 40 weight %. The coating may have a coating weight of, for example, from about 0.1 to about 5% by weight of the carrier, in embodiments from about 0.5 to about 2% by weight of the carrier.

In embodiments, PMMA may optionally be copolymerized with any desired comonomer, so long as the resulting copolymer retains a suitable particle size. Suitable comonomers can include monoalkyl, or dialkyl amines, such as a dimethylaminoethyl methacrylate, diethylaminoethyl methacrylate, diisopropylaminoethyl methacrylate, or t-butylaminoethyl methacrylate, and the like. The carrier particles may be prepared by mixing the carrier core with polymer in an amount from about 0.05 to about 10 percent by weight, in embodiments from about 0.01 percent to about 3 percent by weight, based on the weight of the coated carrier particles, until adherence thereof to the carrier core by mechanical impaction and/or electrostatic attraction.

Various effective suitable means can be used to apply the polymer to the surface of the carrier core particles, for example, cascade roll mixing, tumbling, milling, shaking, electrostatic powder cloud spraying, fluidized bed, electrostatic disc processing, electrostatic curtain, combinations thereof, and the like. The mixture of carrier core particles and polymer may then be heated to enable the polymer to melt and fuse to the carrier core particles. The coated carrier particles may then be cooled and thereafter classified to a desired particle size.

In embodiments, suitable carriers may include a steel core, for example of from about 25 to about 100 microns in size, in embodiments from about 50 to about 75 microns in size, coated with about 0.5% to about 10% by weight, in embodiments from about 0.7% to about 5% by weight, of a conductive polymer mixture including, for example, methylacrylate and carbon black using the process described in U.S. Pat. Nos. 5,236,629 and 5,330,874.

The carrier particles can be mixed with the toner particles in various suitable combinations. The concentrations are may be from about 1% to about 20% by weight of the toner composition. However, different toner and carrier percentages may be used to achieve a developer composition with desired characteristics.

Imaging

The toners can be utilized for electrophotographic processes, including those disclosed in U.S. Pat. No. 4,295,990, the disclosure of which is hereby incorporated by reference in its entirety. In embodiments, any known type of image development system may be used in an image developing device, including, for example, magnetic brush development, jumping single-component development, hybrid scavengeless development (HSD), and the like. These and similar development systems are within the purview of those skilled in the art.

Imaging processes include, for example, preparing an image with a electrophotographic device including a charging component, an imaging component, a photoconductive component, a developing component, a transfer component, and a fusing component. In embodiments, the development component may include a developer prepared by mixing a carrier with a toner composition described herein. The electrophotographic device may include a high speed printer, a black and white high speed printer, a color printer, and the like.

Once the image is formed with toners/developers via a suitable image development method such as any one of the aforementioned methods, the image may then be transferred to an image receiving medium such as paper and the like. In embodiments, the toners may be used in developing an image in an image-developing device utilizing a fuser roll member. Fuser roll members are contact fusing devices that are within the purview of those skilled in the art, in which pressure from the roll may be used to fuse the toner to the image-receiving medium.

In embodiments, the image may be transferred to an image receiving medium such as paper and the like without the use of heat. The transferring of images in this manner may be referred to, in embodiments, as cold pressure fixing and/or cold pressure fusing. In embodiments, a fuser roll member for use in a cold pressure fixing device may apply significant pressure to fuse the toner to the image-receiving medium, without the use of heat. In embodiments, the fuser roll member may apply a pressure of from about 3 kilopounds per square inch (kpsi) to about 10 kpsi, in embodiments from about 5 kpsi to about 9 kpsi, at a temperature of from about 10° C. to about 80° C., in embodiments from about 20° C. to about 50° C., thereby fixing the toner onto the image receiving substrate.

Toners of the present disclosure may exhibit acceptable solid-area rub fix, i.e., the image remains fixed to the substrate and does not smear, at pressures of from about 3 psi (pounds per square inch) to about 11 psi, in embodiments from about 5 psi to about 9 psi, in embodiments about 8 psi. This may be contrasted with a conventional toner which, when fused to a substrate by cold pressure fixing as described above, may exhibit solid-area rub fix at pressures of from about 11 psi to about 16 psi, in embodiments from about 12 psi to about 13 psi.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

Example 1

Polymerization of 11/12-pentadecen-15-olide and Pentadecalactone in a Continuous Packed-bed Reactor.

Pentadecalactone
(Trade name EXALTOLIDE®)

11/12-Pentadecen-15-olide
(Trade name HABANOLIDE®)

A 100-cm long segment of ¼-inch stainless steel tubing was capped at one end and filled with about 70 volume % of about 200-nm glass beads and 30 volume % (about 1 gram) of NOVOZYM® 435 (Novozymes, Denmark) to form the packed bed reactor. NOVOZYM® 435 is an immobilized *Candida antarctica* lipase B resin. The contents of the packed bed reactor were equilibrated in toluene overnight to allow the resin to swell. After equilibration, inlet and outlet feed lines were attached to the packed bed reactor and the packed bed reactor was placed in a heating bath at about 80° C. About 625 ml of 30 weight % monomer solution including a 1:1 mixture of 11/12-pentadecen-15-olide and pentadecalactone in toluene was pumped through the packed bed reactor continuously at a flow rate of about 1.3 ml/min. The product exiting the packed bed reactor was collected and analyzed using gel permeation chromatography (GPC) and differential scanning calorimetry (DSC). After about 30 minutes of operation, the molecular weight of the polymer in the outlet stream became stable ($M_n$=12-14 kg/mol), and the outlet stream was collected continuously for about 8 hours. The eluent was precipitated into methanol, and the resulting white solid was collected by filtration and air-dried, yielding about 180 grams of crystalline polyester with $M_n$=13.6 kg/mol, $M_w$=36.2 kg/mol, and $T_M$=72° C. The overall conversion rate of monomer to polymer was calculated to be about 93%. The catalyst productivity under these conditions was about 180 grams of polymer/gram of catalyst.

Example 2

About 172 grams of the poly(pentadecalactone-co-pentadecenlactone) prepared in Example 1 above was dissolved with about 1.71 grams of succinic anhydride in 400 ml toluene, to which about 5 drops of pyridine had previously been added. The reaction mixture was stirred at about 80° C. for about 16 hours, then was cooled to room temperature and poured into stirring methanol. The resulting white precipitate was filtered and air-dried, providing a polymer with number average molecular weight ($M_N$) of about 15.4 kg/mol, a weight average molecular weight ($M_W$) of about 37.3 kg/mol, a melting temperature ($T_M$) of about 73° C., and an acid value of about 4.15 mg KOH/gram resin.

The dried polymer (about 130 grams) was dissolved in about 950 grams of ethyl acetate that had previously been heated to about 65° C., forming a clear solution (Solution A). Separately, about 6.54 grams DOWFAX™ 2A1 solution (an alkyldiphenyloxide disulfonate from The Dow Chemical Company, containing approximately 3.1 grams DOWFAX™ in water) and about 3 grams aqueous $NH_4OH$ solution were dissolved in about 750 ml of deionized water that had been heated to about 65° C. (Solution B). Solution A was added to Solution B over about 30 seconds, with mixing by an IKA Ultra-Turrax T50 homogenizer. The mixing speed was increased from about 4,000 revolutions per minute (rpm) at the beginning of the Solution A addition step, to about 10,000 rpm at the end of this step. The combined solutions were mixed at about 10,000 rpm for about 30 minutes, after which the mixed suspension was distilled at about 85° C. for about two hours.

The resulting aqueous emulsion was stirred at room temperature overnight in an open vessel, then passed through a 25 µm sieve and centrifuged for about 3 minutes at about 3,000 rpm. The supernatant remaining was decanted, providing about 779 grams of colorless latex (Latex C), with a nominal surfactant loading of about 2.35 parts per hundred (pph). Analysis of Latex C gave the following results: solids loading was about 11.2%; median particle size was about 311 nm; and its acid value was about 6.13 mg KOH/gram resin.

Example 3

Formation of emulsion-aggregation toner. Latex C produced in Example 2 above was used as the crystalline component in a polyester low-melt toner. Latex C was combined with two amorphous resins based on poly(bispropoxy-Bisphenol A-co-fumaric acid/terephthalic acid): the first, hereafter referred to as Latex D, was a resin having a weight average molecular weight (Mw) of about 12 kg/mol, and about 36% solids; the second, hereafter referred to as Latex E, was a resin having a Mw molecular weight of about 75 kg/mol, and about 39% solids. The toner was prepared as follows.

About 93 grams of Latex C, about 107 grams of Latex D, about 98 grams of Latex E, about 47 grams of a polyethylene wax dispersion (IGI Wax, about 29% solids), about 51 grams of a Pigment Blue 15:3 dispersion (from Clariant, about 16% solids), and about 3.2 grams of DOWFAX™ 2A1 surfactant, were mixed with about 480 grams of water, and the resulting mixture was adjusted to a pH of about 3.3 with about 0.3 M nitric acid. The resulting suspension was mixed using an IKA Ultra-Turrax T50 high-shear mixer at about 4,000-5,000 rpm while a mixture of about 2.7 grams aqueous aluminum sulfate (at a concentration of about 28%) and about 72 grams water was added dropwise. The mixture was then slowly heated from room temperature to about 45° C. with stirring, until a particle size of about 5.2 µm was achieved.

A mixture of Latex D (about 58 grams), Latex E (about 54 grams), DOWFAX™ 2A1 surfactant (about 1.8 grams) and water (about 56 grams) was added thereto to form a shell, and heating continued until a particle size of about 5.6 µm had been reached. The pH of the reaction mixture was then adjusted to about 4.5. About 5.8 grams of VERSENE™ 100 chelating agent, an aqueous solution of the tetrasodium salt of ethylenediaminetetraacetic acid (commercially available from Dow Chemical) was added thereto, and the pH further adjusted to about 7.7. The reaction mixture was heated to about 85° C. and held at that temperature for about 3 hours, after which the reaction mixture was poured onto crushed ice. Filtration, washing and drying yielded about 120 grams of particles with a size of about 5.6 µm, a volume average geometric size distribution (GSDv) of about 1.21, a number average geometric size distribution (GSDn) of about 1.31, and a circularity of about 0.93. The sample was referred to as the toner of Example 3.

Electrophotographic Charging Evaluation

Measurement of toner charge (Q/d). Developer samples were prepared by weighing about 0.5 grams of toner onto about 10 grams of electrophotographic carrier in a washed 60 ml glass bottle. Developer samples were prepared in duplicate for each toner that was being evaluated. One sample of the pair was conditioned in the A-zone environment of about 28° C./85% relative humidity (RH), and the other was conditioned in the C-zone environment of about 10° C./15% RH. The samples were kept in the respective environments overnight to fully equilibrate. The following day, the developer was charged by agitating the samples for one hour in a Turbula mixer. The charge on the toner particles was measured using a charge spectrograph (CSG). The toner charge (Q/d) was calculated as the midpoint of the toner charge trace from the CSG. The Q/d was reported in millimeters of displacement from the zero line; in could also be converted to ft/micron by multiplying the value in mm by 0.092. The corresponding Q/m in µC/gram was also measured and included.

Measurement of Toner Charge Maintenance

A developer sample was prepared by weighing about 0.6 grams of toner onto about 10 grams of electrophotographic carrier in a washed 60 ml glass bottle. The developer was conditioned in an A-zone environment of 28° C./85% RH overnight to fully equilibrate. The following day, the developer was charged by agitating the sample for about two minutes in a Turbula mixer. The charge per unit mass (Q/m) of the sample was measured using a tribo blow-off unit. This tribo measurement is made by loading about 0.5 grams of charged developer into a sample holder. The holder is sealed and clamped into the blow-off box where compressed air automatically blows the toner off the carrier. The cage is connected electrically to an electrometer that measures the number of μC off charge that has accumulated. After all the toner is removed in the blow off stage the weight loss is measured and then the charge per unit mass is calculated. The sample was then returned to the A-zone chamber in an idle position. The charge per unit mass measurement was repeated again after about 24 hours. Charge maintenance was calculated from the 24 hour charge as a percentage of the initial charge.

The developer included external charge control additives and a 35 um SCMB carrier. Charge was determined using a charge spectrograph unit. Results relative to a control toner containing a conventional crystalline polyester, are shown below in Table 1.

TABLE 1

| Toner ID | A-zone Q/d | A-zone Q/m | C-zone Q/d | C-zone Q/m | RH Ratio | Charge maintanability 24 hours | Charge maintanability 7 days |
|---|---|---|---|---|---|---|---|
| Control | 9.0 | 31.7 | 15.3 | 47.5 | 0.59 | 91 | 75 |
| Example 3 | 8.4 | 35.9 | 15.1 | 62.9 | 0.56 | 93 | 75 |

Overall, as can be seen in Table 1, charging evaluation for the toner of Example 3 showed similar behavior to the control toner, with slightly higher C-zone Q/m and an acceptable RH ratio.

Electrophotographic Fusing Evaluation

The fusing performance of test samples was evaluated using a DC252 fuser CRU, commercially available from Xerox Corporation, as an off-line fusing fixture. A set of unfused images was first generated using a modified DC 12 printer from XEROX Corporation (with fuser lamps removed). By adjusting the development bias and sending the print through the DC12 printer multiple times, the target toner mass area (TMA) of about 1.00±0.02 mg/cm$^2$ was achieved on the ColorXpressions+90 gsm uncoated paper substrate. Test images were then run through the offline DC252 fusing fixture at a process speed of about 220 mm/second (mm/s) over a range of fuser roll temperatures from about 120° C. to about 210° C. Print gloss was measured using a BYK Gardner 75° gloss meter. A set of six readings (three readings with the gloss meter parallel to the process direction, and 3 readings with the gloss meter perpendicular to the process direction) were measured for each toner at all the test conditions.

Adhesion of toner to paper was then measured by the standard crease area measurement where substrate is folded in half in the area where toner/image is present on the page. A standard crease area tool (metal cylinder, mass=960 grams) was rolled along the folded section. The sheet was then unfolded and fractured toner was removed by wiping the fold with a cotton ball. Using an image analysis system, the amount of toner that had been removed from the paper surface was measured and correlated to crease area standards. The current target crease area measurement (for normal paper) is about 80 CA units or less.

Figure 1:
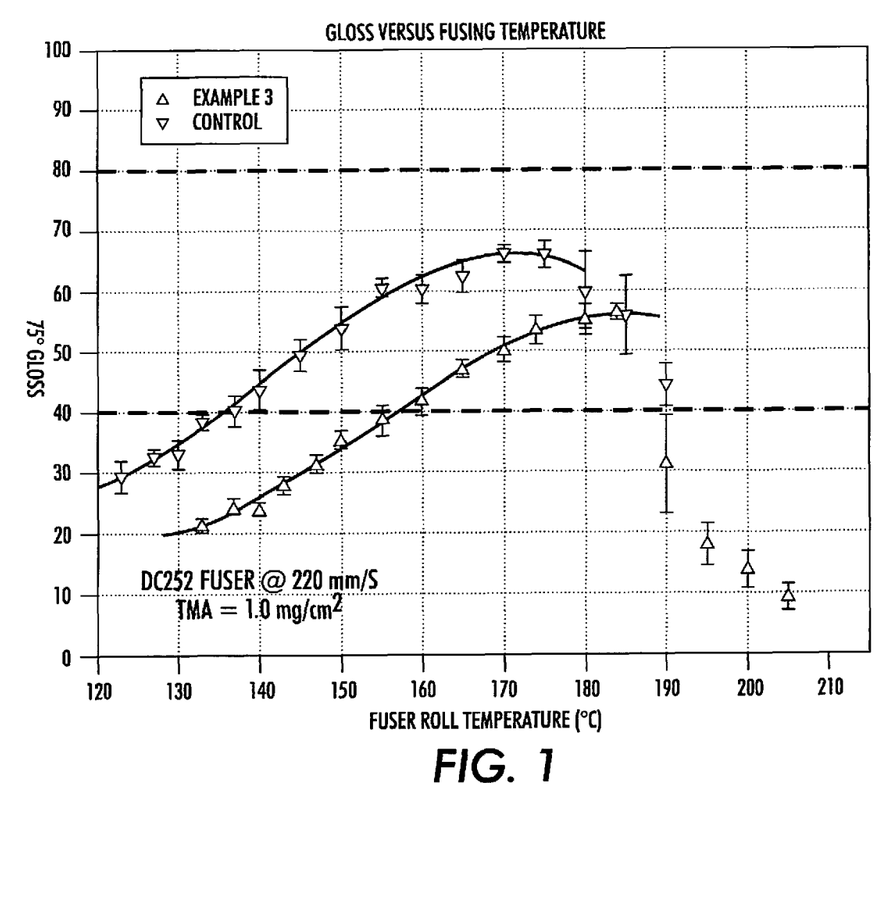
FIG. 1 is a graph of gloss versus fusing temperature for a toner produced in accordance with the present disclosure compared with control toners.
Figure 2:
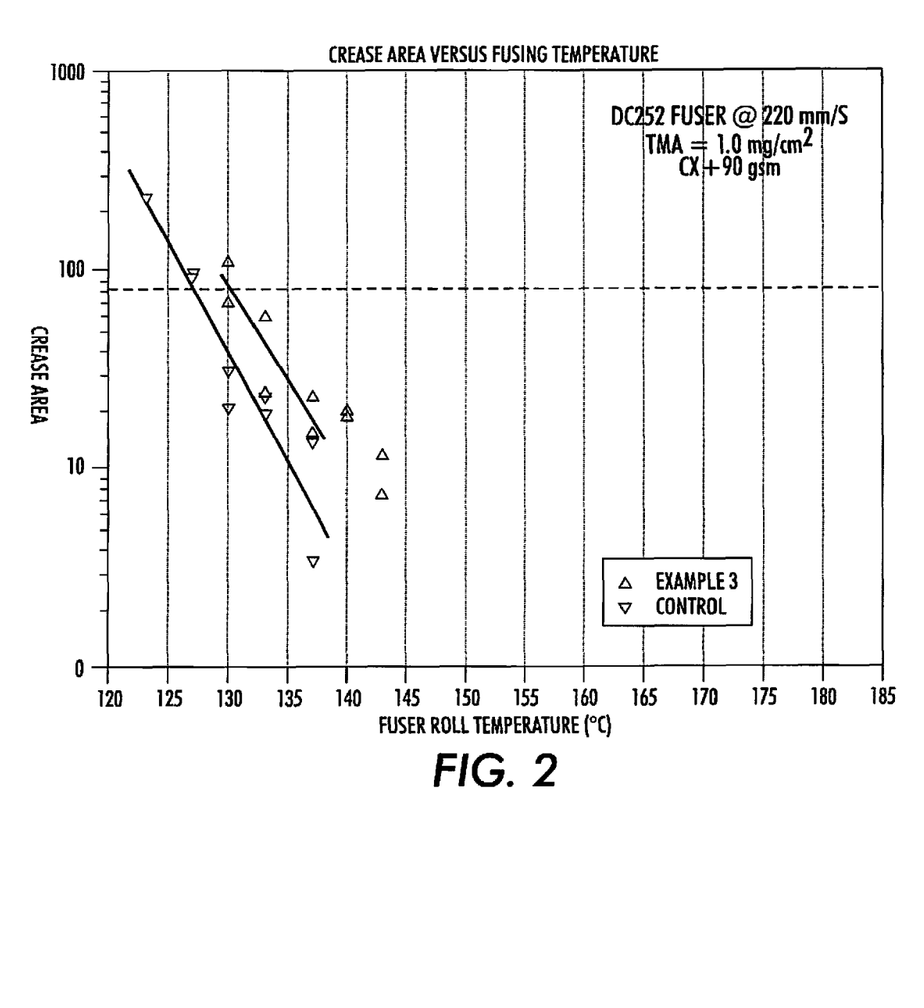
FIG. 2 is a graph of crease area versus fusing temperature for a toner produced in accordance with the present disclosure compared with control toners.

Results of fusing gloss evaluation as a function of temperature for the toner of Example 3, relative to a control toner of similar composition containing a conventional crystalline polyester, and a high-gloss styrene-acrylate toner, are shown in FIG. 1. Results of fusing crease area evaluation as a function of temperature are shown in FIG. 2 relative to the same controls.

Overall, fusing evaluation for the toner of Example 3 showed similar gloss behavior to a high-gloss styrene-acrylate control toner (somewhat lower gloss than a polyester control toner) and similar crease fix behavior to a polyester control toner.

Cold-pressure Fix Evaluation

Cold-pressure fixing of images is of interest as an energy-saving concept in electrophotographic printing. The toner of Example 3 was evaluated for cold-pressure fix by depositing particles on a test sheet and fusing at room temperature in a variable-pressure hydraulic press. The fix quality of the resulting images was assessed at various pressures, by assigning a score from 0 to 10 (0=no fix, 10=perfect fix).

The pressure required to achieve a fix level of 7 with the toner of Example 3 was about 4,000 psi. A control toner containing a conventional crystalline polyester required about 5,000 psi to reach fix level 7, while a commercial toner from DELPHAX, intended for cold-pressure fix applications, required about 3,900 psi to reach this fix level.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A printing apparatus comprising:
    a toner source comprising toner particles; and
    a fuser comprising a fuser roll member capable of applying pressure of from about 3kpsi to about 10 kpsi thereby fixing the toner onto an image receiving substrate at a temperature of from about 10° C. to about 80° C.,
    wherein said toner particles comprise at least one amorphous polyester resin, an optional colorant, an optional wax, and at least one crystalline polyester resin, the at least one crystalline polyester resin is formed by combining at least one component selected from the group consisting of lactones, lactides, cyclic anhydrides, cyclic carbonates, and combinations thereof, with an enzyme selected from the group consisting of lipases, cutinases, and combinations thereof.

2. An apparatus as in claim 1, wherein the toner particles remain fixed to a substrate and do not smear at pressures of from about 3 psi to about 11 psi.

3. An apparatus as in claim 1, wherein the toner particles further comprise a core and a shell, and said shell comprises a resin.

4. An apparatus as in claim 1, wherein the toner particles have a volume average diameter of from about 3 microns to about 25 microns, a Geometric Size Distribution of from about 1.05 to about 1.55, and a circularity of from about 0.90 to about 0.99.

* * * * *